(12) United States Patent
Pardal Filipe et al.

(10) Patent No.: US 9,682,986 B2
(45) Date of Patent: Jun. 20, 2017

(54) PROCESS FOR OBTAINING OPTICALLY ACTIVE PIRLINDOLE ENANTIOMERS AND SALTS THEREOF

(71) Applicant: TECNIMEDE SOCIEDADE TECNICO-MEDICINAL S.A., Sintra (PT)

(72) Inventors: Augusto Eugenio Pardal Filipe, Lisboa (PT); Pedro Filipe Eufrasio Pedroso, Lisboa (PT); Susana Marques Almeida Pecorelli, Alcabideche (PT); Carlos Alberto Eufrasio Casimiro Caixado, Mafra (PT); Ana Sofia da Conceicao Lopes, Milharado (PT); Joao Carlos Ramos Damil, Torres Vedras (PT); Pedro Paulo de Lacerda E Oliveira Santos, Queluz (PT)

(73) Assignee: TECNIMEDE SOCIEDADE TECNICO-MEDICINAL S.A., Sintra (PT)

( * ) Notice: Subject to any disclaimer, the term of this patent is extended or adjusted under 35 U.S.C. 154(b) by 0 days.

(21) Appl. No.: 15/309,906

(22) PCT Filed: May 9, 2014

(86) PCT No.: PCT/PT2014/000027
§ 371 (c)(1),
(2) Date: Nov. 9, 2016

(87) PCT Pub. No.: WO2015/171003
PCT Pub. Date: Nov. 12, 2015

(65) Prior Publication Data
US 2017/0145024 A1    May 25, 2017

(51) Int. Cl.
*C07D 487/06*    (2006.01)
(52) U.S. Cl.
CPC ........ *C07D 487/06* (2013.01); *C07B 2200/07* (2013.01)
(58) Field of Classification Search
CPC .................................................... C07D 487/06
See application file for complete search history.

(56) References Cited

FOREIGN PATENT DOCUMENTS

WO    2015171003 A1    11/2015

OTHER PUBLICATIONS

International Search Report, issued by International Searching Authority in corresponding International Application No. PCT/JP2014/000027, on Nov. 17, 2014.

*Primary Examiner* — Bruck Kifle
(74) *Attorney, Agent, or Firm* — Sughrue Mion, PLLC

(57) ABSTRACT

The present invention provides a new process for obtaining optically active pirlindole enantiomers, in the form of a free base or in the form of pharmaceutically acceptable salts.
The products obtained according to the present invention are enantiomerically pure and are useful in medicine.

17 Claims, No Drawings

PROCESS FOR OBTAINING OPTICALLY ACTIVE PIRLINDOLE ENANTIOMERS AND SALTS THEREOF

The present invention relates to a process for obtaining optically active pirlindole enantiomers, in the form of a free base or in the form of pharmaceutically acceptable salts.

Optically active pirlindole enantiomers according to the present invention are (R)-pirlindole and (S)-pirlindole.

The products obtained according to the present invention are enantiomerically pure and are useful in medicine.

BACKGROUND

Pirlindole, 2,3,3a,4,5,6-hexahydro-1H-8-methyl-pyrazine[3,2,1-j,k]carbazole, is a tetracyclic compound of the formula I

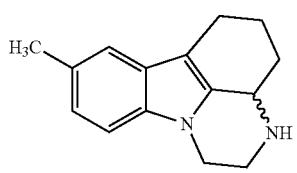

(I)

Pirlindole is a reversible monoamine oxidase A inhibitor being up to date useful as a medicament in the treatment of depression.

Pirlindole has an asymmetric carbon atom which implies that there are two enantiomers, (S)-pirlindole and (R)-pirlindole.

The state of the art teaches several methods for the enantiomeric separation of pirlindole. For example, The Journal of Pharmaceutical and Biomedical Analysis, 18(1998) 605-614, "Enantiomeric separation of pirlindole by liquid chromatography using different types of chiral stationary phases", Ceccato et al, discloses the enantiomeric separation of pirlindole by liquid chromatography (LC) using three different chiral stationary phases.

Further, The Journal of Pharmaceutical and Biomedical Analysis 27(2002) 447-455, "Automated determination of pirlindole enantiomers in plasma by on-line coupling of a pre-column packed with restricted access material to a chiral liquid chromatographic column", Chiap et al., discloses the use of a pre-column packed with restricted access material for sample clean up coupled to a column containing a cellulose based chiral stationary phase for separation and quantitative analysis of the enantiomers.

According to the prior art, Chirality 11:261-266 (1999) all attempts to obtain the enantiomers of pirlindole by selective crystallization with optically active acids failed, and it was only possible to obtain at laboratory scale (few grams) as hydrochloride salt, using derivatization technique in conjunction with preparative chromatography.

The characteristics of the process disclosed in the state of the art limit in a definitive way, its implementation on an industrial or semi-industrial scale due to the necessity to use a separation by chromatography on a large scale which makes the process very costly, difficult to implement and with poor reproducibility.

There is thus a need in the art to find new processes which are viable and of easy industrial application for obtaining enantiomers of pirlindole either in its free base form or as pharmaceutically acceptable salts.

BRIEF DESCRIPTION OF THE INVENTION

According to the present invention, (R)-pirlindole and (S)-pirlindole can be obtained in the form of a free base or in the form of a pharmaceutically acceptable salt, contrary to the teachings of the state of the art, by crystallization of (rac)-pirlindole in the free base form with optically active acids and subsequently allowing its production as free base or as pharmaceutically acceptable salts.

It is therefore an object of the present invention a process for obtaining optically active (R)- and (S)-pirlindole enantiomers, in the form of a free base or in the form of a pharmaceutically acceptable salt characterized by carrying out a resolution by crystallization with optically active acids of (rac)-pirlindole in the free base form.

The optically active pirlindole enantiomers being enantiomerically pure (S)-pirlindole or (R)-pirlindole.

It is therefore a further object of the present invention a process characterized by comprising the following steps:

i) Dissolving (rac)-pirlindole hydrochloride in an aqueous solvent, followed by a subsequent extraction with a chlorinated solvent and complete removal of the solvent to obtain (rac)-pirlindole in the free base form;

ii) Dissolving the (rac)-pirlindole obtained in step i) in an organic solvent, followed by adding an optically active acid for resolution;

iii) Stirring for 15 min to 2 h the suspension formed in ii) while diastereomeric salt precipitation occurs;

iv) Filtering the obtained diastereomeric salt and purifying it by suspension in an organic solvent to obtain (S)-pirlindole or (R)-pirlindole enantiomer in the form of a pharmaceutically acceptable salt formed with the optically active acid; and optionally, v) Obtaining enantiomerically pure (S)-pirlindole and/or (R)-pirlindole as a free base by dissolution of the product obtained in step iv) in an aqueous solvent, subsequent extraction with chlorinated solvent and complete removal of the solvent; and further, optionally, vi) Obtaining S)-pirlindole or (R)-pirlindole in the form of pharmaceutically acceptable acid addition salts by salification of the enantiomerically pure (S)-pirlindole and/or (R)-pirlindole in the form of a free base obtained in step v) with a pharmaceutically acceptable acid to form a pharmaceutically acceptable acid addition salt of S)-pirlindole or (R)-pirlindole enantiomer.

It is also an additional object of the present invention a process as defined previously wherein the optically active acid used in step ii) is selected from the group consisting of: (R)-mandelic acid, (R)-(+)-α-methoxy-α-trifluorophenylacetic acid, (1R,3S)-(+)-camphoric acid, D(+)-malic acid, (S)-mandelic acid, (S)-(−)-α-methoxy-α-trifluorophenylacetic acid, (1S,3R)-(+)-camphoric acid or L (−)-malic acid.

It is also a further object of the present invention a process as defined previously wherein the organic solvent used in steps ii) and iv) is selected from the group consisting of: methanol, ethanol, propanol, 1-butanol, 2-butanol, tert-butyl alcohol, 2-butanone, acetone, ethyl methyl ketone, methyl isobutyl ketone, dimethylsulfoxide, 1,2-dichloroethane, diethyl ether, dimethyl ether, dimethylformamide, methyl tert-butyl ether, 2-propanol, pyridine, toluene, xylene or mixtures thereof in any proportion.

In addition, it is a further object of the invention a process as defined above characterized in that the compound obtained is enantiomerically pure (S)-pirlindole as (R)-mandelate salt, (R)-pirlindole as (S)-mandelate salt, (S)-pirlindole hydrobromide salt, (R)-pirlindole hydrobromide salt, (S)-pirlindole citrate salt, (R)-pirlindole citrate salt, (S)-pirlindole mesylate salt, (R)-pirlindole mesylate salt, (R)-pirlindole (R)-(+)-α-metoxi-α-trifluorophenylacetate salt and (S)-pirlindole R)-(+)-α-metoxi-α-trifluorophenylacetate salt.

DESCRIPTION OF THE INVENTION

According to the present invention, (R)-pirlindole and (S)-pirlindole can be obtained in the form of a free base or in the form of a pharmaceutically acceptable salt, contrary to the teachings of the state of the art, by crystallization of (rac)-pirlindole in the free base form with optically active acids and subsequently allowing its production as free base or as pharmaceutically acceptable salts.

More specifically, according to the present invention, (R)-pirlindole and (S)-pirlindole in the form of a free base or in the form of a pharmaceutically acceptable salt can be obtained by crystallization of (rac)-pirlindole in the free base form with optically active acids in an organic solvent and, optionally its subsequent salification to form pharmaceutically acceptable salts with pharmaceutically acceptable acids.

Applicants have found that under certain specific process conditions, it is indeed possible to carry out the resolution of racemic diastereomeric pirlindole.

The above essential process conditions involve prior isolation of the racemic pirlindole, without which, surprisingly it is not possible to carry out efficiently the resolution, the period of agitation (stirring) after addition of the optically active acid which must be especially controlled to avoid racemization, and the specific type of organic solvent used in the addition phase of optically active acid and purification.

Applicants have found that for short periods of stirring, after addition of the optically active acid to (rac)-pirlindole in the free base form, resolution is ineffective and for longer periods of stirring, racemization occurs.

As a general rule the stirring is carried out during a period that ranges from 15 minutes to 2 hours. Preferably, stirring is performed during a period from 30 minutes to 1 hour.

Applicants have also found that the selection of the specific organic solvent for the optically active acid addition phase (resolution) and purification is quite important because markedly affects the efficiency and yield of the resolution process.

The process of the invention allows obtaining for the first time, (R)-pirlindole and (S)-pirlindole in the form of a free base or a pharmaceutically acceptable salt in amounts that enable to conduct preclinical and clinical studies, in addition to being a process that is easily used on an industrial scale unlike processes known in the art.

The pirlindole molecule has a secondary amine group, which has basic character and thus can form acid addition salts, which are pharmaceutically acceptable salts.

The process described in the present invention allows obtaining (R)-pirlindole and (S)-pirlindole both in its free base form and in the form of pharmaceutically acceptable salts.

For purposes of this invention, it is considered as enantiomerically pure when enantiomeric purity as calculated by chiral chromatography is equal to or greater than 97%.

The process of the invention, when departing from (rac)-pirlindole hydrochloride, comprises the following steps:

i) Dissolving (rac)-pirlindole hydrochloride in aqueous solvent, followed by a subsequent extraction with a chlorinated solvent and complete removal of the solvent to obtain (rac)-pirlindole in the free base form;

ii) Dissolving the (rac)-pirlindole obtained in step i) in organic solvent, followed by adding an optically active acid for resolution;

iii) Stirring for 15 min to 2 h the suspension formed in ii) while diastereomeric salt precipitation occurs;

iv) Filtering the obtained diastereomeric salt and purifying it by suspension in an organic solvent to obtain (S)-pirlindole or (R)-pirlindole enantiomer in the form of a pharmaceutically acceptable salt formed with the optically active acid;

In addition to the detailed process steps, and where the products to be obtained are (S)-pirlindole or (R)-pirlindole enantiomer either as a free base or as a pharmaceutically acceptable acid addition salt with suitable organic and inorganic acids, the said process contemplates optionally at least one of the following steps:

v) Obtaining enantiomerically pure(S)-pirlindole and/or (R)-pirlindole as a free base by dissolution of the product obtained in step iv) in an aqueous solvent, subsequent extraction with chlorinated solvent and complete removal of the solvent; and vi) Obtaining S)-pirlindole or (R)-pirlindole in the form of pharmaceutically acceptable acid addition salts by salification of the enantiomerically pure (S)-pirlindole and/or (R)-pirlindole in the form of a free base obtained in step v) with a pharmaceutically acceptable acid The unit operations performed, the yields obtained, the absence of steps in difficult conditions (eg; high temperatures) and especially no need to use separation by chromatography make this process particularly suitable for industrial use and as such unique and different compared to the prior art.

For the purpose of the present invention, the term "pharmaceutically acceptable salt" refers to those salts which are, within the scope of sound medical evaluation, suitable for use in contact with the tissues and organs of humans and lower animals without displaying toxicity, irritation, allergic response and the like and are commensurate with a reasonable benefit/risk ratio. Pharmaceutically acceptable salts include those pharmaceutically acceptable acid addition salts formed with organic and inorganic acids and those pharmaceutically acceptable salts formed with optically active acids according to the present invention.

Representative acid addition salts include, but are not limited to, acetate, adipate, alginate, citrate, aspartate, benzoate, benzenesulfonate, bisulfate, butyrate, camphorate, camphorsulfonate, digluconate, fumarate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Non-limiting examples of acids that can be used to form pharmaceutically acceptable acid addition salts with the compounds of the invention include inorganic acids such as hydrochloric acid, hydrobromic acid (HBR) sulfuric acid and phosphoric acid and organic acids such as citric acid, anhydrous citric acid, mandelic acid, succinic acid and methanesulfonic acid.

For the purpose of the present invention, "optically active acids" include (S)-mandelic acid, (R)-mandelic acid, (R)-(+)-α-methoxy-α-trifluorophenylacetic acid, (S)-(−)-α-methoxy-α-trifluorophenylacetic acid, (1S,3R)-(−)-camphoric acid, (1R,3S)-(+)-camphoric acid, L-(−)-malic acid, D-(+)-malic acid, or similarly well known in the art optically active acids.

For the purposes of the present invention the term "aqueous solvent" refers to water or mixtures of water with other organic solvents, in which water is the main component, i.e., is present in an amount not inferior to 95% (v/v).

For purposes of this invention the term "organic solvent" refers to solvents commonly used in organic chemistry or mixtures thereof in any proportions.

Non-limiting examples of organic solvents used in steps ii) and iv) of the process of the present invention are selected from the group consisting of: methanol, ethanol, propanol, 1-butanol, 2-butanol, tert-butyl alcohol, 2-butanone, acetone, ethyl methyl ketone, methyl isobutyl ketone, dimethyl sulfoxide, 1,2-dichloroethane, diethyl ether, dimethyl ether, dimethylformamide, methyl tert-butyl ether, 2-propanol, pyridine, toluene, xylene and the like, and mixtures thereof in any proportion.

Preferred are the following solvents: ethanol, methanol, 1-butanol, 2-butanol, tert-butyl alcohol, acetone, methyl ethyl ketone and isopropanol as well as mixtures thereof in any proportions, such as isopropanol/acetone (1:1), ethanol/acetone (1:1), ethanol/methyl isobutyl ketone (1:1) and ethanol/1-butanol (1:4).

For purposes of this invention the term "chlorinated solvent" means chloroform, dichloromethane, methylene chloride, trichloromethane or carbon tetrachloride, or mixtures thereof in any proportions.

Compounds obtained according to the present invention are:
(S)-pirlindole (S)-mandelate;
(S)-pirlindole (R)-mandelate;
(S)-pirlindole (R)-(+)-α-methoxy-α-trifluorophenylacetate;
(R)-pirlindole hydrobromide;
(R)-pirlindole mesylate;
(S)-pirlindole citrate;
(R)-pirlindole citrate;
(R)-pirlindole (free base);
(S)-pirlindole (free base);

Examples of other compounds obtainable by the process of the invention are:
(S)-pirlindole hydrobromide
(S)-pirlindole mesylate
(S)-pirlindole benzenesulfonate
(R)-pirlindole p-toluenesulfonate
(S)-pirlindole bisulfate
(R)-pirlindole oxalate
(R)-pirlindole maleate
(S)-pirlindole acetate
(S)-pirlindole glutamate
(S)-pirlindole lactate
(R)-pirlindole adipate
(R)-pirlindole benzoate
(S)-pirlindole malate

EXAMPLES

The examples below are intended to illustrate the invention and should not be construed as limiting thereof.

Example 1

(R)-pirlindole (S)-mandelate 100 g (0.38 mole) of (R,S)-pirlindole hydrochloride were dissolved in 16 L deionized water at room temperature. To the solution 42.4 g (0.4 mole) of anhydrous sodium carbonate were added and the contents were stirred for 1 h.

The above solution was extracted with 3×4 L of dichloromethane and the combined organic phases were dried over sodium sulfate and evaporated under vacuum to dryness.

To the concentrate was added 2 L of acetone.

To the above solution was added, under stirring, a solution of 27.6 g (0.18 mole) of (S)-mandelic acid in 150 ml of acetone.

Stirring was continued during 45 minutes.

The precipitated product was filtered, washed with 2×100 mL of acetone and dried under vacuum at 35° C.-45° C.

The above product was suspended in ethanol (250 mL) and was subsequently filtered and dried under vacuum at 35° C.-45° C., yielding 48.5 g (0.13 mole) of (R)-pirlindole (S)-mandelate, (yield—68%). Chiral HPLC (enantiomeric purity=98.2%).

Example 2

(S)-pirlindole (R)-mandelate

Using the same procedure as in Example 1 (except that the stirring time after addition of the chiral acid was 60 min), starting from 100 g (0.38 mole) of (R,S)-pirlindole hydrochloride and using 27.6 g (0.18 mole) of (R)-mandelic acid, yielded 45.6 g (0.12 mole) of (S)-pirlindole (R)-mandelate (yield=63%). Chiral HPLC (enantiomeric purity=98.7%).

Example 3

(S)-pirlindole (R)-mandelate

Using the same procedure as in Example 1, except that a mixture of isopropanol/acetone (1:1) was used as the organic solvent and the stirring time after addition of the chiral acid was 35 min, starting from 10 g (0.038 mole) of (R,S)-pirlindole hydrochloride and using 2.8 g (0.018 mole) of (R)-mandelic acid, yielded 4.1 g (0.011 mole) of (S)-pirlindole (R)-mandelate (yield=57.9%). Chiral HPLC (enantiomeric purity=98.1%).

Example 4

(S)-pirlindole (R)-(+)-α-methoxy-α-trifluorophenyl acetate

Using the same procedure as in Example 1, except that a mixture of ethanol/acetone (1:1) was used as the organic solvent, the stirring time after addition of the chiral acid was 55 min and as optically active acid, (R)-(+)-α-methoxy-α-trifluorophenylacetic acid (8.3 g) (0.018 mole) was used, starting from 10 g (0.038 mole) of (R,S)-pirlindole hydrochloride, yielded 4.8 g (0.010 mole) of (S)-pirlindole (R)-(+)-α-methoxy-α-trifluorophenylacetate (yield=52.6%). Chiral HPLC (enantiomeric purity=97.7%).

Example 5

(R)-Pirlindole hydrobromide

The product obtained in Example 1 (10 g, 0.027 mole) was dissolved in 550 ml of deionized water. The aqueous phase was extracted with 3×300 ml of chloroform. The combined organic phases were dried over sodium sulfate, evaporated to dryness under vacuum and 200 ml of acetone were added.

To the above solution, under stirring, a solution of 6 ml of HBr (48% aqueous solution) (0.04 mole) was added.

The dried precipitated product is filtered, washed with 2×10 ml of acetone and dried under vacuum at 35° C.-45° C.

The above product was suspended in ethanol/methyl isobutyl ketone (1:1) (250 mL) and was subsequently filtered and dried under vacuum at 35° C.-45° C., yielding 6.5 g (0.021 mole) of (R)-pirlindole hydrobromide (yield=77.8%). Chiral HPLC (enantiomeric purity=97.9%).

Example 6

(R)-Pirlindole citrate

The product obtained in Example 1 (10 g, 0.027 mole) was dissolved in 550 ml of deionized water. The aqueous phase was extracted with 3×300 ml of trichloroethane. The combined organic phases were dried over sodium sulfate, evaporated to dryness under vacuum and 200 ml of acetone were added.

To the above solution, under stirring 7.7 g of anhydrous citric acid (0.04 mole) were added.

The dried precipitated product was filtered, washed with 2×10 ml of acetone and dried under vacuum at 35° C.-45° C.

The above product was suspended in etanol/1-butanol (1:4) (250 mL) and was subsequently filtered and dried under vacuum at 35° C.-45° C., yielding 9.2 g (0.020 mole) of (R)-pirlindole citrate (yield=74.1%). Chiral HPLC (enantiomeric purity=97.6%).

Example 7

(R)-Pirlindole mesylate

Starting from 10 g of (R)-pirlindole (S)-mandelate obtained in Example 1 and following the procedure described in Example 5 using methanesulfonic acid as pharmaceutical acceptable acid, 7.4 g (0.023 mole) of (R)-pirlindole mesylate were obtained (yield=85.2%). Chiral HPLC (enantiomeric purity=98.0%).

Example 8

(S)-pirlindole hydrobromide

Starting from 10 g of (S)-pirlindole (R)-mandelate obtained in Example 2 using hydrobromic acid as pharmaceutical acceptable acid, and following the procedure described in Example 6, 7.4 g (0.024 mole) of (S)-pirlindole hydrobromide were obtained (yield=88.9%). Chiral HPLC (enantiomeric purity=98.2%).

Example 9

(S)-pirlindole mesylate

Starting from 10 g of (S)-pirlindole (R)-mandelate obtained in Example 2 and following the procedure described in Example 6 using methanesulfonic acid as pharmaceutical acceptable acid, 6.8 g (0.021 mole) of (S)-pirlindole mesylate were obtained (yield=77.8%). Chiral HPLC (enantiomeric purity=98.0%).

Example 10

(S)-Pirlindole citrate

Starting from 10 g of (R)-mandelate of (S)-pirlindole obtained in Example 2 and following the procedure described in Example 6 using citric acid as pharmaceutical acceptable acid, 9.5 g (0.021 mole) of (R)-pirlindole citrate were obtained (yield=77.8%). Chiral HPLC (enantiomeric purity=98.5%).

Example 11

(R)-pirlindole (Free Base)

The product obtained in Example 1 (2 g, 0.005 mole) was dissolved in 110 ml of deionized water. The aqueous phase was extracted with 3×75 ml of dichloromethane. The combined organic phases were dried over sodium sulfate, evaporated under vacuum until complete removal of the solvent and placed at 0° C./5° C. overnight. Crystallization occurred. 1.1 g (0.0049 mole) of ((R)-pirlindole (free base) were obtained (yield=98%). Chiral HPLC (enantiomeric purity=98.3%).

Example 12

(S)-pirlindole (Free Base)

The product obtained in Example 2 (2 g, 0.005 mole) was dissolved in 110 ml of deionized water. The aqueous phase was extracted with 3×75 ml of trichloroethane. The combined organic phases were dried over sodium sulfate, evaporated under vacuum until complete removal of the solvent and placed at 0° C./5° C. overnight. Crystallization occurred. 1.1 g (0.0049 mole) of (S)-pirlindole (free base) were obtained (yield=98%). Chiral HPLC (enantiomeric purity=97.8%).

The invention claimed is:

1. A process for obtaining optically active pirlindole enantiomers, in the form of a free base or in the form of a pharmaceutically acceptable salt comprising:
   carrying out a resolution by crystallization with optically active acids of (rac)-pirlindole in the free base form.

2. The process according to claim 1, wherein the optically active pirlindole enantiomers are enantiomerically pure (S)-pirlindole or (R)-pirlindole.

3. The process according to claim 1 comprising the following steps:
   i) Dissolving (rac)-pirlindole hydrochloride in an aqueous solvent, followed by a subsequent extraction with a chlorinated solvent and complete removal of the solvent to obtain (rac)-pirlindole in the free base form;
   ii) Dissolving the (rac)-pirlindole obtained in step i) in an organic solvent, followed by adding an optically active acid for resolution;
   iii) Stirring for 15 min to 2 h the suspension formed in ii) while diastereomeric salt precipitation occurs;
   iv) Filtering the obtained diastereomeric salt and purifying it by suspension in an organic solvent to obtain (S)-pirlindole or (R)-pirlindole enantiomer in the form of a pharmaceutically acceptable salt formed with the optically active acid; and optionally, v) Obtaining enantiomerically pure (S)-pirlindole and/or (R)-pirlindole as a free base by dissolution of the product obtained in step iv) in an aqueous solvent, subsequent extraction with chlorinated solvent and complete removal of the solvent; and, optionally, vi) Obtaining S)-pirlindole or (R)-pirlindole in the form of pharmaceutically acceptable acid addition salts by salification of the enantiomerically pure (S)-pirlindole and/or (R)-pirlindole in the form of a free base obtained in step v) with a pharmaceutically acceptable acid to form a pharmaceutically acceptable acid addition salt of S)-pirlindole or (R)-pirlindole enantiomer.

4. The process according to claim 1 wherein the optically active acid used in step ii) is selected from the group consisting of: (R)-mandelic acid, (R)-(+)-α-methoxy-α-trifluorophenylacetic acid, (1R,3S)-(+)-camphoric acid, D (+)-malic acid, (S)-mandelic acid, (S)-(−)-α-methoxy-α-trifluorophenylacetic acid, (1S,3R)-(+)-camphoric acid or L (−)-malic acid.

5. The process according to claim 1 wherein the organic solvent used in steps ii) and iv) is selected from the group consisting of: methanol, ethanol, propanol, 1-butanol, 2-butanol, tert-butyl alcohol, 2-butanone, acetone, ethyl methyl ketone, methyl isobutyl ketone, dimethylsulfoxide, 1,2-dichloroethane, diethyl ether, dimethyl ether, dimethylformamide, methyl tert-butyl ether, 2-propanol, pyridine, toluene, xylene or mixtures thereof in any proportion.

6. The process according to claim 1 wherein the compound obtained is enantiomerically pure (S)-pirlindole as (R)-mandelate salt.

7. The process according to claim 1 wherein the compound obtained is enantiomerically pure (R)-pirlindole as (S)-mandelate salt.

8. The process according to claim 1 wherein the compound obtained is enantiomerically pure (S)-pirlindole hydrobromide salt.

9. The process according to claim 1 wherein the compound obtained is enantiomerically pure (R)-pirlindole hydrobromide salt.

10. The process according to claim 1 wherein the compound obtained is enantiomerically pure (S)-pirlindole citrate salt.

11. The process according to claim 1 wherein the compound obtained is enantiomerically pure (R)-pirlindole citrate salt.

12. The process according to claim 1 wherein the compound obtained is enantiomerically pure (S)-pirlindole mesylate salt.

13. The process according to claim 1 wherein the compound obtained is enantiomerically pure (R)-pirlindole mesylate salt.

14. The process according to claim 1 wherein the compound obtained is enantiomerically pure (R)-pirlindole R)-(+)-α-metoxi-α-trifluorophenylacetate salt.

15. The process according to claim 1 wherein the compound obtained is enantiomerically pure (S)-pirlindole R)-(+)-α-metoxi-α-trifluorophenylacetate salt.

16. The process according to claim 1 wherein the compound obtained is enantiomerically pure (R)-pirlindole in the free base form.

17. The process according to claim 1 wherein the compound obtained is enantiomerically pure (S)-pirlindole in the free base form.

* * * * *